United States Patent
Porat

(10) Patent No.: US 6,624,198 B1
(45) Date of Patent: Sep. 23, 2003

(54) AIDS PROPHYLACTIC LUBRICATING COMPOSITION AND DEVICES FOR ITS USE

(75) Inventor: Michael Porat, Afeka (IL)

(73) Assignee: Medgreen, Inc., Fairfield, NJ (US)

( * ) Notice: Subject to any disclaimer, the term of this patent is extended or adjusted under 35 U.S.C. 154(b) by 0 days.

(21) Appl. No.: 07/978,671

(22) PCT Filed: Feb. 5, 1993

(86) PCT No.: PCT/US93/00826

§ 371 (c)(1), (2), (4) Date: Nov. 7, 1994

(87) PCT Pub. No.: WO93/15728

PCT Pub. Date: Aug. 19, 1993

(30) Foreign Application Priority Data

Feb. 6, 1992 (IL) .................................................. 100881

(51) Int. Cl.⁷ ............................................. A61K 31/155
(52) U.S. Cl. ..................................................... 514/635
(58) Field of Search ......................................... 514/635

(56) References Cited

U.S. PATENT DOCUMENTS 5,342,617 A * 8/1994 Gold .......................... 424/405

OTHER PUBLICATIONS

Shinkai et al 82CA:52123E 1975.*
Harbison et al 111CA 4062E 1989.*
Suzuki et al 115CA 239679H 1991.*
Remington Plan Sees 17ᵗʰ ed 1985 pp 1158,1167,1168, 1298.*

* cited by examiner

*Primary Examiner*—Russell Travers
(74) *Attorney, Agent, or Firm*—Dennison, Schultz & Dougherty

(57) ABSTRACT

A prophylactic spermicidal lubricant composition and method for its use in safe sexual relations, including prevention of infection by HIV and other viruses. The composition contains:

a) a cosmetically acceptable lubricant effective to reduce friction, thereby reducing the rupture of blood vessels during sexual relations;

b) an effective amount of chlorhexidine salt active against HIV and other, viruses, the chlorhexidine salt immobilizing sperm and reacting with vaginal mucosa to form a barrier to the penetration of sperm calls into the uterus, but also destroying natural flora in the vagina and thereby permitting growth of fungi which causes ulceration; and c) an effective amount of a cosmetically acceptable fungicide to prevent the growth of fungi in the vagina in the absence of natural bacterial flora, destroyed by the chlorhexidine salt.

13 Claims, 1 Drawing Sheet

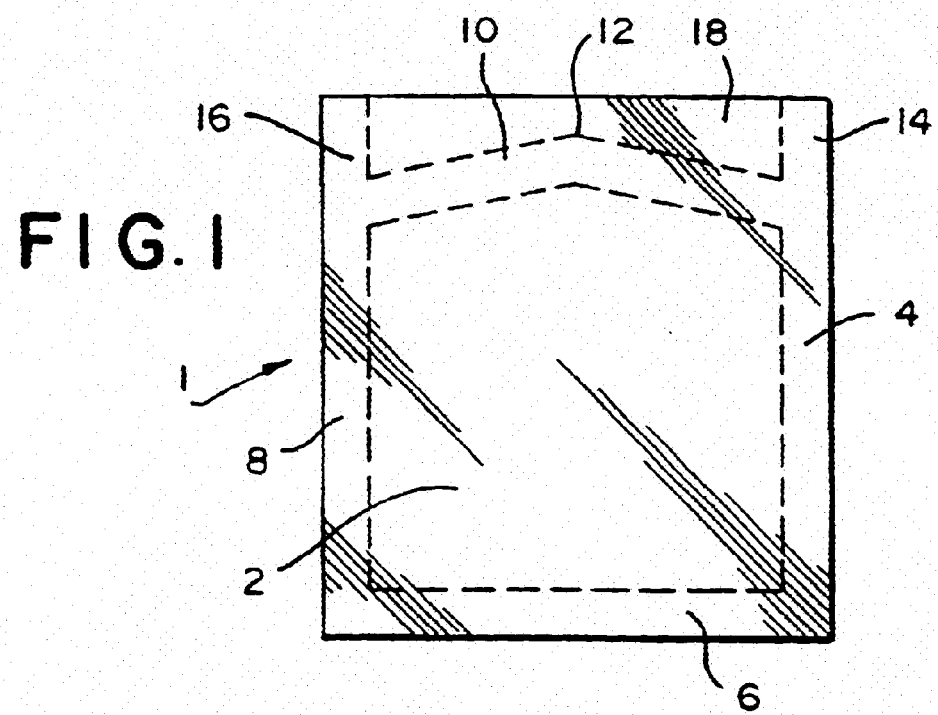

AIDS PROPHYLACTIC LUBRICATING COMPOSITION AND DEVICES FOR ITS USE

This application is a 371 of PCT/US93/00826 filed Feb. 5, 1993 which claims priority from Israel Patent Application 100881 filed Feb. 6, 1992.

FIELD OF THE INVENTION

The present invention relates to an antiseptic lubricant composition for use in sexual relations. The lubricant composition of this invention reduces the risk of infection by lethal viruses such as herpes simplex (HSC), cytomegalovirus (CMB), influenza A, parainfluenza, hepatitis B (HBV) and particularly human immunodeficiency virus (HIV). The lubricant composition of this invention, in addition to destroying bacteria and viruses, prevents pregnancy by destroying sperm cells and furthermore prevents any surviving sperm cells from entering the uterus. The present invention also relates to a method for reducing the risk of infection by lethal viruses during sexual relations and reducing the risk of pregnancy, and to devices containing antiseptic lubricant.

BACKGROUND OF THE INVENTION

In the last decade, the rapid spread of the HIV and the accompanying concern of its terrifying consequences for mankind, have created a sense of urgency to find both short and long term solutions for this modern plague. There are many ways in which the HIV and some other viruses are transmitted by people. One of the most common forms of transmission is by sexual contact. During intercourse, there are basically three ways in which the HIV can be transmitted from one person to another. One way is by the friction caused by a penis penetrating into the vagina, which is capable of tearing small and sometimes invisible blood vessels (capillary vessels) of both sexual partners. The blood from these vessels is consequently commingled and the HIV present in one partner is transferred via the blood to the other partner. As far as is known, the HIV develops mainly in the blood cells, although it is transferred and transmitted by body fluids. A second way for transmitting the HIV is through the body fluids which the body secretes during sexual relations. A third way is via the semen. It has been found that the HIV can reside in the spermatophore (sperm-liquid) or even on or in the spermatocide (sperm cell). Thus, the HIV which resides in the sperm may infect the other sexual partner.

HIV, herpes and similar viruses are surrounded by three envelopes. These envelopes are composed of the same material as that of the human cell walls. When the outside envelope of the virus comes into contact with the outer cell wall of humans, the human cell recognizes the virus as part of itself and absorbs it, and proceeds to produce more viruses until they overflow. The excess viruses are then expelled from the human cell and search for other host cells which will continue to produce more viruses.

The most common and so far most effective way of avoiding infection by HIV and other related viruses during sexual relations is by the use of a condom put on prior to copulation. The condom prevents direct contact between sexual organs and body fluids of the partners and also retains the sperm and prevents it from entering the vagina and eventually the uterus. As far as is known, the HIV cannot penetrate the rubber material from which condoms are made. Only if the condom is defective, for example perforated or otherwise damaged, can transmission of the virus occur.

Many people, however, do not like using a condom, mainly because of the odd sensation of indirect contact with the sex partner, which in many cases interferes with and/or diminishes sexual satisfaction.

It is also known that to increase sexual satisfaction during intercourse, people avail themselves of lubricants which may be soluble, like K-Y (a Trademark product of Johnson & Johnson) or a non-soluble fatty lubricant, like soft paraffin. This is particularly the case with atrophy and in elderly people, who use lubricants to complement the diminished quantities of natural lubricants produced as compared with the situation in younger people.

Gels and foams for application before or during sexual intercourse are known, some of which contain spermicides, such as Nonoxynol-9. Many disinfectants are also known to be effective against viruses and are used as antiseptics in topical applications in concentrations that are not harmful to body tissues. Some compositions containing disinfectants are also known for use in disinfecting the sexual organs. These disinfectants, however, have never been used in concentrations sufficient to effectively kill viruses, specifically the HIV virus, in lubricant compositions for use in sexual relations. The disinfectant compositions are generally used as antiseptics and applied topically for destroying bacteria and/or viruses that already exist in the area to which they are applied and to maintain these areas free of such organisms, to prevent possible future infections such as in the treatment of wounds and burns. Among the known disinfectants are the previously mentioned Nonoxynol-9, Benzalkonium Chloride, Povidone Iodine, Nitrofurazone and chlorhexidine salt. These disinfectants, and others not mentioned but found in medical pharmacopoeias, have similar disinfecting characteristics, although they differ chemically and react differently to body tissues. Many of these disinfectants destroy bacteria as well as viruses. Most of them, however, do not destroy fungi. This presents a problem, since the flora of bacteria prevent the growth of fungi and with the destruction of the bacteria, there is a tendency for the fungi to develop.

One of the problems of using a disinfecting agent in the area of the female genitals is that the tissues in the vagina are normally regenerated frequently and antiseptic agents in general inhibit the vaginal tissues from regenerating.

It is the object of the present invention to provide a prophylactic lubricating composition for use in sexual relations.

It is a further object of the invention to enhance sexual satisfaction during intercourse, to solve the problem of infection, and to avoid pregnancy, by using a single prophylactic lubricating composition which will accomplish the following:

1. Provide proper lubrication.
2. Destroy bacteria and viruses.
3. Prevent the mobility of sperm cells.
4. Prevent the penetration of sperm cells into the uterus.
5. Prevent fungi from developing in the vagina.
6. Safe use without side effects.

Yet another object of the invention is to provide devices containing and dispensing a prophylactic lubricating composition and a method for using the same.

A still further object of the present invention is to provide a prophylactic method for protecting against the spread of infection from bacteria and viruses such as HIV during sexual relations, as well as avoid becoming pregnant, for people who do not use condoms or diaphragms during intercourse, or provide an additional prophylactic safety factor for those who do use them.

DETAILED DESCRIPTION OF THE INVENTION

In accordance with the present invention, there is provided a prophylactic lubricant composition for use during sexual relations, comprising an effective lubricant and an antiseptic compound effective in destroying the human immunodeficiency virus and other viruses, said antiseptic compound being a spermacide, which also reacts with the vaginal mucosa to form a barrier to the penetration of sperm cells into the uterus, said composition having no substantial detrimental side effects. In a preferred embodiment, the prophylactic lubricant composition also contains a fungicide, a preferred fungicide being methylparaben.

The lubricant may be any effective lubricant or combination of lubricants acceptable for cosmetic applications.

The antiseptic compounds in accordance with this invention are preferably chlorhexidine and its salts, particularly the gluconate or digluconate salts.

Chlorhexidine and its salts are well described in the medical literature as effective against a wide range of viruses and bacteria and have been used in the form of antiseptic solutions, creams and gels for topically disinfecting wounds, skin, mouth, urethra and other parts of the body. Chlorhexidine is known not to accumulate in the blood and does not enter the mammalian cells. When applied to the human genitals in concentrations even up to 4%, it did not produce any undesirable side effects.

During ovulation, the female body produces a mucous in the cervix which selectively allows sperm cells to penetrate to the uterus. At all other times, the cervix does not allow penetration of sperm cells or semen into the uterus. Chlorhexidine, on the other hand, diffuses into the cervical mucous, creating a suspension. This suspension restricts the penetration of sperm cells during ovulation and causes them to rapidly lose their mobility. This occurs at concentrations of chlorhexidine in excess of 0.1%. Thus, by using chlorhexidine as the active antiseptic compound in accordance with the present invention, the chlorhexidine diffuses into the cervical mucous prior to the ejection of semen and in effect creates the "sealed bag" of the vagina, which will retain all the body secretions including the semen. Any viruses present will be destroyed by the chlorhexidine.

Chlorhexidine, in concentrations above 0.1%, effectively destroys the envelope of thee virus and in so doing prevents the virus from penetrating the human cell. The present invention is premised on the discovery that when selected antiseptically active materials are incorporated in lubricants for use in sexual relations, a number of advantages are obtained which make the sexual relations safe and worry-free, both from the fear of contracting a serious viral disease such as the HIV, and the fear of becoming pregnant. The antiseptic material for use in this invention must be effective in concentrations that are safe and acceptable for use in contact with sexual organs. It must have the ability to kill bacteria and viruses at such concentration levels. It must have spermacidal properties and furthermore must have the additional feature of reaction with vaginal mucosa to seal the cervical passage against penetration of any residual or surviving sperm cells.

Medical and pharmaceutical studies have shown that the HIV develops mainly in the blood cells and is carried by various body fluids to other cells. When the antiseptic lubricant of this invention is applied to the sex organs, a number of advantages are obtained. The lubricant reduces the friction between the penis and the vaginal wall, thus reducing the rupture of blood cells which might otherwise occur and therefore reducing the amount of blood that is commingled. Any blood that does appear is immediately disinfected by the active antiseptic ingredient. Furthermore, the antiseptic compound also kills any bacteria and viruses in the body fluids which are present or are generated during intercourse. The selected antiseptic compound, being a spermacide as well, destroys the sperm and any virus it may carry inside the vagina, and last but not least, the antiseptic compound reacts with the mucosa to create a barrier in the cervix, preventing any surviving sperm from entering the uterus. Thus, in accordance with the present invention, the vagina is converted into a "sealed bag" by creating a barrier which prevents sperm from passing through the cervix and any viruses present in the sealed vagina will subsequently be destroyed.

The tissues in the vagina are normally regenerated frequently and antiseptic agents are known to often inhibit the vaginal tissues from regenerating. Therefore lubricating compositions for use in the area of the vagina should have the same pH as the vagina itself, in order to eliminate this problem. The antiseptic lubricant composition of this invention should also preferably contain an alcohol or mixtures of alcohols, to enhance the activity of the disinfectant. Preferably water soluble lubricants are used, since any stains that they may form on clothing or sheets are readily washed out with water and their use is particularly recommended when rubber or latex prophylactics are used, such as condoms or diaphragms. The preferred lubricant is propylene glycol, but other water soluble lubricating materials, as known in the art, such as glycerine, may also be used, alone or in combination. Although water soluble lubricants are preferred, fatty lubricants like soft paraffin may also be used if desired. The antiseptic lubricant composition preferably contains a fungicide such as methylparaben. This particular fungicide is body friendly, does not harm tissues and destroys fungi which develop in the absence of bacterial flora. However, other known and approved fungicides may also be used. In the case where the active antiseptic compound also is a fungicide, it is not required to include a separate fungicide in the lubricant composition.

Compositions for use by people having oral sex can also be prepared by adding a flavour, such as menthol, lemon, cherry or other desired flavour.

A preferred antiseptic lubricant composition in accordance with this invention comprises a mixture of propylene glycol or glycerine, or both, with water, mixed with carbomethyl cellulose (CMC) or hydroxyethyl cellulose (HEC) or both. These are formulated with chlorhexidine gluconate or digluconate and methylparaben. Such a composition can have the following concentrations:

| | |
|---|---|
| Chlorhexidine salt | 0.1% to 5% |
| Methylparaben | 0.1% to 1.0% |
| Propylene glycol | 2.0% to 6% |
| Glycerine | 5.0% to 15% |
| CMC or HEC | 0.5% to 2.0% |
| Purified water | To complete to 100% |

A preferred lubricant composition has the following concentration of ingredients:

| | |
|---|---|
| Chlorhexidine digluconate | 0.2% to 0.6% |
| Methylparaben | 0.15% |
| Propylene glycol | 4.0% |
| Glycerin | 11.0% |
| HEC | 1.25% |
| Purified water | To complete to 100% |

The lubricant composition should be easy to apply and should not disturb the sexual act, without diminishing the antiseptic potency. (Most disinfectants are sensitive to light and should be packaged in sealed containers protected from light and air). It is therefore suggested to package the lubricant in a single use disposable sterile sealed packet. Sterilization can take place by heating the sealed packet for ten hours at 70° C. to give a S.A.L. of $10^{-10}$.

BRIEF DESCRIPTION OF THE DRAWINGS

The present invention will be further understood and appreciated from the following detailed description taken in conjunction with the drawings, in which:

FIG. 1 illustrates a disposable sealed packet for holding sterilized disinfecting gel;

FIG. 2 illustrates a diaphragm with a disinfecting lubricant impregnated foam;

FIG. 3 illustrates a diaphragm with a disinfecting lubricant capsule; and

FIG. 4 shows a squeeze bottle container for holding a lubricating composition in accordance with the invention.

Referring now to FIG. 1, there is shown a packet 1 for holding the lubricant composition of this invention. The packet 1 comprises two approximately square sheets 2 sealed together by hot stamping around the edges of the packet. Edges 4, 6 and 8 are sealed at the end of the sheets, whereas the top of the packet is sealed with a chevron seal 10, with an apex 12. The seal on edges 4 and 8 extend to the top of the packet 14 and 16 beyond the upper chevron seal 10, thus leaving the upper edge of the packet 18 unsealed, so that the two sheets forming the packet can be separated with the fingers. The sheets comprising the packet are preferably made of aluminum foil or polyester and have a peelable lacquer on their inner surface to facilitate sealing and separation of the non-sealed areas when the packet is opened. The packet is of course light and air-impermeable and materials for preparing such similar packets are known in the art.

The packet is used in the following manner. The upper edges 18 of the packet are peeled apart, opening the seal first at the apex 12 and then the entire seal 10, completely opening the packet while the leaving the side and bottom edges completely sealed. The upper sealing edges 14 and 16 prevent the peeling of the packet sheets along the side edges 4 and 8, thus creating a sachet. A penis can now be inserted into the open packet and immersed in the lubricant composition. Alternatively, the lubricating composition contained in the open packet can be spread with the fingers on to the sexual organs.

Devices for use by the female for applying lubricant compositions are illustrated in FIGS. 2–4. FIGS. 2 and 3 illustrate a diaphragm 20 which has foam sponge 22 adhering to the centre of the diaphragm and which is impregnated with the antiseptic lubricant composition of this invention (FIG. 2). Alternatively, a capsule 24, containing lubricant composition, can be adhered to the centre of the diaphragm 20 (FIG. 3). When the diaphragm is inserted into the vagina, its outer edges 26 and 28 surround the outer edges of the cervix, blocking the entrance to the uterus. A penis pushing against the diaphragm will first press against the sponge 22 or burst open capsule 24 to release the disinfecting lubricant composition, which will then destroy any bacteria and viruses coming in contact therewith.

Referring now to FIG. 4, there is shown a squeezable accordion type cylinder 30 having a length of approximately 5 cm and a diameter of approximately 2.5 cm, generally made of an opaque plastic having a nozzle 31 with a fitted removable cap 33. Prior to copulation, the female removes the cap 33 from the nozzle 31 and inserts the nozzle into the vagina, squeezing the accordion type cylinder 30 to release the antiseptic lubricant composition into the vagina. The composition being in a gel form, it remains in the vagina during intercourse, enabling the antiseptic compound to destroy any bacteria and viruses present or introduced by the male partner.

Other means for dispensing the lubricant composition are available, such as towelettes preimpregnated with lubricant, which can be used to spread or coat the penis or wipe the vagina, or capsules or pessaries containing the lubricant composition.

For maximum safety, it is suggested that the lubricant composition of the present invention be used together with other prophylactic means, such as condoms or diaphragms, to provide an additional safety margin, in case the conventional devices are defective. Furthermore, the increased lubrication provided by the composition of this invention is an additional benefit from its use. The antiseptic lubricant can also be used by doctors and in hospitals to lubricate gloves or instruments before examining the vagina, rectum or mouth.

What is claimed is:

1. A method for reducing vaginal ulcer facilitated HIV transmission and providing for safe sexual relations with protection comprising applying to the sexual organs prior to sexual relations a paraben based fungicide containing spermicidal lubricant to prophylactically treat chlorohexidine inducted fungal vaginal ulcers comprising a) a cosmetically acceptable lubricant effective to reduce friction, thereby reducing the rupture of blood vessels during sexual relations;

b) an effective amount of chlorhexidine salt active against HIV and other viruses, said chlorhexidine salt immobilizing sperm and reacting with vaginal mucosa to form a barrier to the penetration of sperm cells into the uterus, said chlorhexidine salt destroying the natural flora in the vagina, thereby permitting growth of fungi which causes ulceration of the vagina creating a source for HIV penetration into the bloodstream; and c) an effective amount of a cosmetically acceptable fungicide to prevent,the growth of fungi in the vagina in the absence of natural bacterial flora destroyed by the chlorhexidine salt;
   said composition having no substantial side effects.

2. A method as in claim 1, wherein the chlorhexidine salt is a gluconate or digluconate salt.

3. A method as in claim 1, wherein the lubricant is selected from the group consisting of propylene glycol, glycerin and mixtures thereof.

4. A method as in claim 1, wherein the fungicide is methylparyben.

5. A method as in claim 1, wherein the composition has a natural pH corresponding to that of the vagina.

6. A method as in claim 1, wherein the composition further comprises an alcohol.

7. A method as in claim 1, wherein the composition is water soluble.

8. A method as in claim 6, wherein the composition comprises:

| | |
|---|---|
| Chlorhexidine salt | 0.1 to 5% |
| Methylparaben | 0.1 to 1.0% |
| Propylene glycol | 2.0 to 6% |
| Glycerin | 5.0 to 15% |
| CMC-or HEC | 0.5 to 2.0% |
| Purified Water | to 100%. |

9. A method as in claim 6, wherein the composition comprises:

| | |
|---|---|
| Chlorhexidine digluconate | 0.2 to 0.6% |
| Methylparaben | 0.15% |
| Propylene glycol | 4.0% |
| Glycerin | 11.0% |
| HEC | 1.25% |
| Purified Water | to 100%. |

10. A method as in claim 1, wherein the composition further comprises a food grade flavoring material.

11. A method as in claim 10, wherein the flavoring material is selected from the group consisting of menthol, lemon and cherry.

12. A method as in claim 1, wherein the composition is impregnated in a towlette, sponge or capsule.

13. A method as in claim 1, wherein the composition is in the form of a pessary.

\* \* \* \* \*